(12) United States Patent
Dahle

(10) Patent No.: US 6,667,045 B2
(45) Date of Patent: Dec. 23, 2003

(54) TOPICAL APPLICATIONS FOR SKIN TREATMENT

(76) Inventor: Joseph Scott Dahle, 550 W. 350 North, #3, Tremonton, UT (US) 84337

( * ) Notice: Subject to any disclaimer, the term of this patent is extended or adjusted under 35 U.S.C. 154(b) by 268 days.

(21) Appl. No.: 09/410,674

(22) Filed: Oct. 1, 1999

(65) Prior Publication Data

US 2002/0039591 A1 Apr. 4, 2002

(51) Int. Cl.⁷ ............... A61K 6/00; A61K 7/00; A61K 7/06; A01N 25/00
(52) U.S. Cl. ............ 424/401; 424/70.1; 514/844; 514/861
(58) Field of Search .............. 424/70.1, 401; 514/938, 861, 844

(56) References Cited

U.S. PATENT DOCUMENTS

| | | | |
|---|---|---|---|
| 3,948,943 A | 4/1976 | Eberhardt et al. ...... 260/326.45 |
| 4,564,522 A | 1/1986 | Rocke ...................... 424/195.1 |
| 4,610,978 A | 9/1986 | Dikstein et al. ............... 514/46 |
| RE33,107 E | 11/1989 | Dikstein et al. ............... 514/46 |
| 5,006,337 A | 4/1991 | Motitschke et al. ...... 424/195.1 |
| 5,276,061 A * | 1/1994 | DeLuca et al. |
| 5,512,200 A | 4/1996 | Garcia ........................ 252/142 |
| 5,658,956 A | 8/1997 | Martin et al. ................ 514/724 |
| 5,665,364 A * | 9/1997 | McAtee et al. |
| 5,674,912 A | 10/1997 | Martin ........................ 514/724 |
| 5,703,041 A | 12/1997 | Afriat et al. .................... 514/2 |
| 5,811,083 A | 9/1998 | Pelle et al. .................... 424/59 |
| 5,952,373 A * | 9/1999 | Lanzendorfer et al. ...... 514/152 |

OTHER PUBLICATIONS

Hawley, G. G., Ed., 'The Condensed Chemical Dictionary', 10th Ed., Van Nostrand Reinhold Co., New York, (1981):431–432.*

* cited by examiner

*Primary Examiner*—Sreeni Padmanabhan
*Assistant Examiner*—Lauren Q. Wells
(74) *Attorney, Agent, or Firm*—Kirton & McConkie; Michael F. Krieger

(57) ABSTRACT

The present invention discloses a topical composition consisting of combinations of mineral oil, vegetable shortening, vitamin E, purified water and other ingredients to form useful therapeutic, dermatological, pharmaceutical, medical or cosmetic compositions for treatment of skin maladies and disorders, namely eczema.

6 Claims, No Drawings

TOPICAL APPLICATIONS FOR SKIN TREATMENT

BACKGROUND

1. Field of the Invention

The present invention relates generally to the field of skin care products and more particularly to topical skin applications for treatment of skin disorders and maladies. The present invention may be embodied in creams, lotions, oils, sprays and other typical dosage forms for direct application to the skin.

2. Background

Skin maladies and disorders have plagued mankind for centuries. They range from temporary dry skin caused by environmental conditions to serious illnesses which can cause incapacitation and death. Included in this range are dry skin, severe dry skin, dermatitis, psoriasis, eczema, terosis, dandruff, ichthyosis, keratoses, pruritis, age spots, cradle cap, lentigines, scales, melasmas, wrinkles, stretch marks, dermatoses, minor burns and erythema.

These maladies and disorders can be treated in a number of ways including oral ingestion of drugs, injection of drugs, dietary modification, topical applications and other therapeutic methods. Of these treatment methods, the one most preferable and convenient to patients is generally a topical application.

SUMMARY AND OBJECTS OF THE INVENTION

The compounds of the present invention can be formulated into suitable therapeutic, dermatological, pharmaceutical, medical, and/or cosmetic compositions depending on the particular use for which it is to be used. For example, cosmetic or therapeutic, or both.

Preferred embodiments of the present invention comprise a combination of vegetable oil, mineral oil, vitamin E and water along with other ingredients. These compositions provide relief from itching and inflammation and moisturize the skin as well. They also promote the healing of rashes, numerous skin disorders and types of skin atrophy.

Accordingly, it is an object of the some embodiments of the present invention to provide a composition and method for moisturizing skin.

It is another object of some embodiments of the present invention to provide a composition and method for relieving inflammation of the skin.

It is a further object of some embodiments of the present invention to provide a composition and method for promoting healing of damaged skin.

It is yet another object of some embodiments of the present invention to provide a composition and method for relieving skin itch.

DETAILED DESCRIPTION OF THE PREFERRED EMBODIMENTS

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

The most preferred mode of administration for treating the skin disorders described above is topical. The compounds of the present invention can be formulated into suitable therapeutic, dermatological, pharmaceutical, medical, and/or cosmetic compositions depending on the particular use for which it is to be used. For example, cosmetic or therapeutic, or both.

Preferred embodiments of the present invention comprise a combination of vegetable oil, mineral oil, vitamin E and sterile water along with other ingredients. These compositions provide relief from itching and swelling, moisturize skin and promote the healing of rashes and skin disorders.

The compositions of some embodiments of the present invention may contain additional ingredients such as carrier, solvent, excipient or vehicle ingredients. These may include, by way of example and not by way of limitation, water, acetone, ethanol, ethylene glycol, propylene glycol, butane-1,3-diol, acrylates copolymers, isopropyl myristate, isopropyl palmitate, mineral oil, butter(s), aloe, talc, botanical oils, botanical juices, botanical extracts, botanical powders, other botanical derivatives, lanolin, urea, petroleum preparations, tar preparations, plant or animal fats, plant or animal oils, soaps, triglycerides, and keratin(s). Mixtures formed by the combination of the above ingredients to form soaps, lotions, tinctures, creams, pastes, emulsions, gels/jellies, aerosols, sprays or ointments which are non-toxic and pharmaceutically, medically, dermatologically, and/or cosmetically acceptable may also be comprised within embodiments of the present invention.

Additionally, moisturizers, sunscreens, fragrances, dyes, thickening agents such as paraffin, jojoba, paba, and waxes, surfactants, humectants, occlusives, hygroscopic agents, emulsifiers, emollients, lipid-free cleansers, antioxidants and lipophilic agents, maybe added to the present compositions if desired.

In addition to these and other vehicles, it shall be understood that the therapeutic, dermatological, pharmaceutical, medical, and/or cosmetic compositions of the present invention may include other ingredients such as those that improve or eradicate itching, irritation, pain, inflammation, age spots, keratoses, wrinkles, and other blemishes or lesions of the skin. By way of example and not by way of limitation, analgesics, anesthetics, antiacne agents, antibacterial agents, anti-yeast agents, anti-fungal agents, antiviral agents, antibiotic agents, porbiotic agents, anti-protozal agents, anti-pruritic agents, antidandruff agents, anti-dermatitis agents, anti-emetics, anti-inflammatory agents, anti-hyperkeratolyic agents, anti-dry skin agents, antiperspirants, anti-psoriatic agents, anti-seborrheic agents, hair conditioners, hair treatments, hair growth agents, anti-aging agents, anti-wrinkle agents, antihistamine agents, disinfectants, skin lightning agents, depigmenting agents, vitamins and vitamin derivatives, gamma-linolenic acid (GLA), beta carotene, quercetin, asapalene, melaluca alternifolia, dimethicone, neomycin, corticosteroids, tanning agents, zinc/zinc oxides, sulfur agents, hormones, retinoids, clotrimazole, ketoconazole, miconazole, griseofulvin, hydroxyzine, diphenhydramine, pramoxine, lidocaine, procaine, mepivacaine, monobenzone, erythidocaine, erythromycin, tetracycline, clindamycin, meclocline, hydroquinone, minocycline, naproxen, ibuprofen, theophylline, cromolyn, alburterol, retinoic acid and its derivatives, hydrocortisone and its derivatives, mornetasone, desonide, trimcinolone, predisolone, NUTRACORT® brand topical steroid application, salicylic acid, phospholipids, calamine, allantoin, isohexadelane, ceresin, galcipotriene, DOVONEX® brand dermatological preparation, anthralin, betamethasone valerate, betamethasone diproprionate, trimcinolone acetonide, fluocinonide, clobetasol propionate, benzoyl peroxide, crotamition, propranolon, promethanzine, vitamin A palmitate, vitamin E acetate, vitamin D and mixtures or derivatives thereof may be added to embodiments of the present invention to improve or alter their effectiveness.

The compounds of the present invention may be used as their therapeutic, dermatological, pharmaceutical, medical, and/or cosmetic acceptable salts. Such salts may be prepared from pharmaceutically and chemically acceptable non-toxic acids or bases including inorganic and organic acids and inorganic and organic bases. Such salts may contain, by way of example and not by way of limitation, the following ions: Acetate, benzensulfonate, benzoate, camphorsulfonate, citrate, fumarate, gluconate, hydrobromide, hydrochloride, lactate, maleate, mandelate, mucate, nitrate, pamoate, phosphate, succinate, sulfate, tartate, pyruvate and the like. Such salts may also contain the following cations: aluminum, calcium, lithium, magnesium, potassium, sodium, zinc, benzathine, chloroprocaine, choline, diethanolamine, ethylenediamine, meglumine and procaine.

An embodiment of the present invention comprising 85% vegetable shortening, 8% mineral oil, 2% vitamin E and 5% purified water was tested on patients diagnosed with eczema. Results related in the following examples show surprisingly successful results in alleviating the chief complaints of a broad cross-section of patients.

EXAMPLE 1

A male patient, age 7, diagnosed with eczema on the neck and legs. Topical application of the present invention in cream form relieved skin irritation, relieved itching, softened skin, and cleared up the rash. Other medications such as DIPROLENE® brand topical corticosteroid preparation did not provide complete relief.

EXAMPLE 2

A male patient, age 7, diagnosed with eczema on the shoulders, arms, hands and buttocks. Topical application of the present invention in cream form relieved skin irritation, relieved itching, softened skin and completely cleared up the rash. Other medications such as BAG BALM® brand ointment, AVON ® brand cosmetic Moisturizing Therapy Cream and DIPROLENE® brand topical corticosteroid preparation did not provide complete relief.

EXAMPLE 3

A male patient, age 5, diagnosed with eczema on the face, shoulders, arms, hands, upper and lower back, chest, stomach, legs and feet. Topical application of the present invention in cream form relieved skin irritation, healed the open wounds and softened the skin. Other medications such as TRIDESILON® brand skin ointment, Triamcinolone, Lac-hydra did not provide complete relief.

EXAMPLE 4

A female patient, age 23, diagnosed with eczema on the neck, arms and hands. Topical application of the present invention in cream form relieved skin irritation, relieved itching, softened skin, and cleared up the rash. Other medications such as cortisone and siocon did not provide complete relief.

EXAMPLE 5

A female patient, age 23, diagnosed with eczema on the neck and legs. Topical application of the present invention in cream form relieved skin irritation, relieved itching, softened skin, and cleared up the rash.

EXAMPLE 6

A female patient, age 27, diagnosed with eczema on the arms, hands and legs. Topical application of the present invention in cream form relieved skin irritation, relieved itching, softened skin, and cleared up the rash.

EXAMPLE 7

A male patient, age 12, diagnosed with eczema on the face, arms, hands, and feet. Topical application of the present invention in cream form relieved skin irritation, relieved itching, softened skin, and cleared up the rash.

Preferred embodiments of the present invention comprise the following ingredients which are listed according to their percentage by weight in relation to the total weight of the composition.

| COMPOSITION 1 | |
|---|---|
| Vegetable Shortening | about 15% to about 90% |
| Mineral Oil | about 5% to about 40% |
| Vitamin E | about 1% to about 20% |
| Sterile Water | about 2% to about 35% |

| COMPOSITION 2 | |
|---|---|
| Vegetable Shortening | about 30% |
| Mineral Oil | about 30% |
| Vitamin E | about 25% |
| Purified Water | about 15% |
| Additional ingredient A | about 2% |
| Additional ingredient B | about 3% |

| COMPOSITION 3 | |
|---|---|
| Vegetable Shortening | about 30% |
| Mineral Oil | about 28% |
| Vitamin E | about 20% |
| Purified Water | about 15% |
| Anti-inflammatory agent | about 7% |

| COMPOSITION 4 | |
|---|---|
| Vegetable Shortening | about 30% |
| Mineral Oil | about 28% |
| Vitamin E | about 20% |
| Purified Water | about 15% |
| Anti-itch agent such as hydrocortizone | about 7% |

| COMPOSITION 5 | |
|---|---|
| Vegetable Shortening | about 30% |
| Mineral Oil | about 28% |
| Vitamin E | about 20% |
| Purified Water | about 15% |
| Sunscreen | about 7% |

| COMPOSITION 6 | |
|---|---|
| Vegetable Shortening | about 30% |
| Mineral Oil | about 28% |
| Vitamin E | about 20% |
| Purified Water | about 15% |
| anesthetic ingredient | about 7% |

| COMPOSITION 7 | |
|---|---|
| Vegetable Shortening | about 30% |
| Mineral Oil | about 28% |
| Vitamin E | about 20% |
| Purified Water | about 15% |
| fragrance | about 7% |

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed:

1. A topical skin care composition for treatment of eczema consisting of:
    about 30% by weight vegetable shortening;
    about 28% by weight mineral oil;
    about 20% by weight vitamin E;
    about 20% by weight water; and
    about 3% by weight tetracycline.

2. A topical skin care composition for treatment of eczema consisting of:
    about 30% by weight vegetable shortening;
    about 28% by weight mineral oil;
    about 20% by weight vitamin E; and
    about 15% by weight water.

3. A pharmaceutical cream consisting of:
    about 20% to about 90% by weight vegetable shortening;
    about 5% to about 50% by weight mineral oil;
    about 1% to about 15% by weight vitamin B; and
    about 2% to about 20% by weight water,
        wherein said pharmaceutical cream is applied topically to the skin specifically for treatment of the skin condition eczema.

4. A method for treating the skin condition eczema comprising topically applying the composition of claim 1 to an area of skin affected by eczema.

5. A method for treating the skin condition eczema comprising topically applying the composition of claim 2 to an area of skin affected by eczema.

6. A method for treating the skin condition eczema comprising topically applying the composition of claim 3 to an area of skin affected by eczema.

* * * * *